United States Patent [19]
Taylor

[11] Patent Number: 6,139,879
[45] Date of Patent: Oct. 31, 2000

[54] FUNGICIDAL AND BACTERICIDAL COMPOSITIONS FOR PLANTS CONTAINING COMPOUNDS IN THE FORM OF HEAVY METAL CHELATES

[75] Inventor: John B. Taylor, DeLand, Fla.

[73] Assignee: Foliar Nutrients, Inc., Cairo, Ga.

[21] Appl. No.: 09/387,100

[22] Filed: Aug. 31, 1999

Related U.S. Application Data

[63] Continuation-in-part of application No. 08/881,968, Jun. 25, 1997, abandoned.
[51] Int. Cl.$^7$ .......................... A01N 59/20; A01N 59/16; A01N 31/00; A01N 33/00; A01N 37/00
[52] U.S. Cl. .......................... 424/630; 424/617; 424/638; 424/639; 424/641; 424/650; 424/DIG. 6; 514/492; 514/493; 514/494; 514/499; 514/500; 514/557; 514/561; 514/567; 514/568; 514/570; 514/646; 514/649; 514/667; 514/669; 514/673; 514/728; 514/736; 514/738; 514/741; 514/836
[58] Field of Search .................................... 424/617, 630, 424/638, 639, 641, 646, 650, DIG. 6, 405; 514/492, 493, 494, 499, 502, 974, 836, 557, 561, 567, 568, 570, 646, 667, 669, 673, 728, 736, 738, 741, 649, 500

[56] References Cited

U.S. PATENT DOCUMENTS

| | | | |
|---|---|---|---|
| 2,921,847 | 1/1960 | Knell et al. | 71/1 |
| 3,852,444 | 12/1974 | D'Amico | 425/245 |
| 4,041,164 | 8/1977 | Albrecht et al. | 424/263 |
| 4,517,362 | 5/1985 | Muller et al. | 546/7 |
| 4,714,614 | 12/1987 | Scher | 424/93.47 |
| 5,152,820 | 10/1992 | Dawson et al. | 71/27 |
| 5,342,980 | 8/1994 | Haley | 556/117 |

FOREIGN PATENT DOCUMENTS

| | | | |
|---|---|---|---|
| 93/08971 | 5/1993 | WIPO . | |

OTHER PUBLICATIONS

Aboulroos,'Reaction of EDTA, DTPA, and EDDHA complexes of Zinc, Copper, and Manganese with a Calcareous Soil' (1981), Journal of Plant Nutrition and Soil Science, vol. 144, No. 2, pp. 164–173.

Skrzypczak et al.,'Effect of some fertilizers chelates on the growth of pathogenic fungi and development of disease symptoms on host plants II.' (1996), Phytopathol. Polonica 11, pp. 41–50.

Krajncic et al.,'Promotion of flowering by Mn–EDDHA in the photoperiodically neutral plant *Spirodela polyrrhiza* (L.) Schleiden' (1995), J. Plant Physiol., vol. 147 (3/4), pp. 397–400.

McCaslin et al.,'Fertilization of common bermudagrass *Cynodon dactylon* L. with foliar applications of iron' (1977), N.M., Agric. Exp. Stn., Res. Rep., 334, pp. 1–4.

Kannan et al., 'A study of the cytoplasmic and vacuolar accumulation of iron and manganese in excised wheat roots' (1976), Commun. Soil Sci. Plant Anal., vol. 7, No. 9, pp. 763–775.

Ramani et al.,'Studies on zinc uptake and influence on zinc and iron on chlorophyll development in young maize cultivars' (1985), J. Plant Nutr., vol. 8, No. 12, pp. 1183–1189.

Ramani et al.,'An examination of zinc uptake patterns by cultivars sorghum and maize: differences amongst hybrids and their parents' (1985), J. Plant Nutr., vol. 8, No. 12, pp. 1199–1210.

Ramani et al., 'Studies on translocation of zinc in bean plants evidence for retransolcation during new growth'(1985), J. Plant Physiol., vol. 121, No. 4, pp. 313–318.

Nabhan et al., 'Chelate behavior in saline–alkaline soil conditions' (1977), Plant Soil, vol. 46, No. 3, pp. 603–618.

Goetticher et al.,'HPLC analysis of metal chelating agents in micronutrients' (1995), Fresenius' J. Anal. Chem., 352 (3–4), pp. 398–400.

Matocha et al.,'Efficacy of fungicidal and nutritional treatments on cotton root rot suppression' (1997), 1997 Proceedings Beltwide Cotton Conferences, New Orleans, LA, USA, Jan. 6–10, National Cotton Council, vol. 1, pp. 135–137.

Karacal et al.,'Effect of Zn on yield and qualtiy of rice in Turkey' (International Rice Research Newsletter (1986) vol. 11, No. 6, pp. 29–30), STN/CAS online, file CABA, abstract.

*Primary Examiner*—John Pak
*Assistant Examiner*—Frank Choi
*Attorney, Agent, or Firm*—Lathrop & Cage L.C.

[57] ABSTRACT

The present invention relates to heavy metal chelate compositions, which are used as fungicides and bactericides, and methods of using the compositions. In particular, the present invention relates to a chelate, that is an EDDHA (copper-ethylenediamine-di-o-hydroxyphenylacetic acid), combined with a heavy metal, including iron, tin, zinc, manganese, copper, and combinations thereof.

2 Claims, 4 Drawing Sheets

FUNGICIDAL AND BACTERICIDAL COMPOSITIONS FOR PLANTS CONTAINING COMPOUNDS IN THE FORM OF HEAVY METAL CHELATES

The present patent application is a continuation-in-part of patent application Ser. No. 08/881,968, filed Jun. 25, 1997, now abandoned.

FIELD OF INVENTION

The present invention is broadly concerned with fungicidal and bactericidal compositions, and methods of use, which provide improved efficacy in controlling fungus and bacterial infections in plants. More particularly, the compositions and methods relate to heavy metal chelates, and preferably to a copper chelate in the form of Cu-EDDHA (copper ethylenediamine-di-o-hydroxyphenylacetic acid), in aqueous solution.

BACKGROUND OF INVENTION

Fungicides, as well as bactericides, are either chemical or biological agents used to protect agricultural crops from infectious pathogens which, if left uncontrolled, result in the weakening or destruction of a plant. In regards to agricultural crops, this is unacceptable, as economic losses will result. Specific pathogens which tend to have an undesired effect on various agricultural crops include Citrus Greasy Spot, Citrus Melanose, Oak Leaf Blister, Erwinia, Xanthomonas, and Alternaria. In the interest of protecting valuable agricultural crops, it is desired to have a fungicide and bactericide composition that readily eliminates or treats these various plant maladies, as well as other infectious agents.

Copper (Cu) compounds that are active as fungicides and bactericides have been in agricultural use since the advent of Bordeaux in the grape vineyards of France in the early 1800s. It has been observed that various types of copper compounds can be used to effectively treat various plant pathogens. As such, many different formulations of fungicides employing copper compounds, such as wettable powders, water based flowables, and dry flowables, are commonly used today in modern agricultural applications. While copper compounds are known to impart desirable fungicidal and bactericidal properties, there are associated problems. Specifically, known copper compounds are typically either phytotoxic, non-soluble, or ineffective as a fungicide or bactericide.

Generally, copper compounds used as fungicides have, for the most part, been inorganic in form when applied to agricultural uses. The inorganic copper compounds have been used because they have been observed to be non-phytotoxic. Organic forms of the copper compounds, while beneficially water soluble, have been found to be generally phytotoxic, especially in foliar applications.

Water soluble, copper compounds such as $CuSO_4$, though effective to inhibit germination of fungus spores, cannot be used in foliar applications to agricultural crops because the cupric ion is extremely phytotoxic. Therefore, relatively insoluble forms of inorganic copper compounds, such as cupric hydroxide, have been found to be more effective fungicides. Note, however, that not all water insoluble Cu compounds are fungicidal or bactericidal. It is known that the in-vitro fungicidal activity is largely dependent on the copper solubility in the spore exudate and in the fungal cell. Also, despite the phytotoxicity, certain organic copper compounds have some utility as fungicides. An example of a suitable organic copper compound is CUTRINE (Cu salt of tri-ethanole amine) which is quite effective as an aquatic algicide, but unsuitable for use in other foliar applications.

While inorganic copper compounds are beneficially non-phytotoxic, they generally suffer from low water solubility. Modern day agricultural uses of inorganic copper compounds as fungicides employ varying forms of copper compounds having relatively low water solubility and include, for example, cupric hydroxide, tri basic copper sulfate, and tank mix combinations (with heavy metal ethylene-bis-di-thiocarbamate fungicides to enhance the bactericidal activity against certain important agricultural bacterial such as Xanthomonas, Pseudomonas, and Erwinia). The lack of solubility of the inorganic copper compounds is an undesired problem. Because known and popular copper fungicides are largely water insoluble, they are normally applied in relatively large volume aqueous suspensions and, as such, are readily removed by rain after application. Frequent applications are, thus, necessary at short intervals—an application process which is expensive and environmentally imprudent.

Thus, both forms, inorganic and organic, suffer from problems. Therefore, the need exists for a highly water soluble Cu compound based fungicide and bactericide that is not phytotoxic. A need also exists for a water soluble Cu compound based fungicide and bactericide that reduces the adverse Cu load on the plant, thus reducing the non-target impact to the environment. Further, a need exists for such fungicidal and bactericidal compounds that permit use of other heavy metals such as manganese, zinc, iron, copper and mixtures thereof, as may be desired for specific fungicidal or bactericidal properties.

SUMMARY OF INVENTION

The present invention relates to a heavy metal chelate fungicide and bactericide composition and methods of using the composition. Preferably, the chelate is a composition that is a member of the EDDHA (ethylenediamine-di-o-hydroxyphenylacetic acid) family, and the metal is selected from the group consisting of iron, copper, manganese, zinc, tin, and combinations thereof. Copper, however, is the most preferred metal. Importantly, the present invention addresses the problems discussed before, of solubility, phytotoxicity, and effectiveness. In particular, the heavy metal chelate fungicide and bactericide composition provides an improved antifungal and antibacterial composition for use on plants that contains, as active ingredients, fungicidally and bactericidally effective amounts of the heavy metal chelates in aqueous solution. It has been observed that the application of the heavy metal chelate composition to a plant substantially eliminates fungus and bacteria disease. Not only is the composition effective in eliminating fungus and bacteria, but it is substantially non-phytotoxic. Also, the heavy metal chelate is soluble in aqueous solution. Thus, the composition provides for protection of plants against fungal and bacterial infections without the attendant phytotoxicity.

Importantly, the heavy metal chelate composition is a singular product that imparts antifungal and antibacterial protection upon application without being excessively phytotoxic. The heavy metal chelate composition is, additionally, environmentally safe, comparatively inexpensive to use, and has low mammalian toxicity.

Essentially, the present antifungal and bacterial composition is comprised of an active material, a fungicidally effective amount of a heavy metal chelate, and an agriculturally acceptable carrier, such as water. The preferred fungicidal and bactericidal compositions is comprised of water and a heavy metal chelate selected from the group consisting of Fe-EDDHA (iron ethylenediamine-di-o-hydroxyphenylacetic acid), Cu-EDDHA, Mn-EDDHA, Zn-EDDHA, Sn-EDDHA, and mixtures thereof. Other family members of EDDHA can be substituted therefor, including pEDDHA and EDDHMA. Desirably, both antifungal and antibacterial effects are achieved with one composition.

When applied to a plant, the heavy metal chelate composition should be applied to a field or other area where agricultural crops are grown in an amount equal to from about 0.01 to about 2.0 pounds of Active Ingredient (AI) per acre and, more preferably, between 0.01 and 0.05 lbs of AI.

DETAILED DESCRIPTION

The present invention relates to a composition that is both a fungicide and a bactericide and a method for using such composition. The composition is advantageously useful in eliminating or at least substantially reducing the effects of infection by various fungal and bacterial plant pathogens. The composition is a heavy metal chelate in aqueous solution, with it preferred that the chelate be a member of the EDDHA family of compositions. The heavy metal attached to the chelate can be selected from any of a variety of row 4 or 5 metal constituents.

As stated, the present composition is comprised of a heavy metal chelate and an amount of water to form an aqueous composition. The heavy metal chelate can be formed by a known process, with the reaction summarized as reacting an amount of metal chloride hexahydrate with water and an amount of mono-amide di-hydrochloride in a reaction vessel. A catalyst, such as sodium hydroxide, is then added which will cause formation of the metal oxide EDDHA. Among the metal hexahydrates that can be reacted with the mono-amide di-hydrochloride are iron, zinc, tin, manganese, and copper. The resulting heavy metal chelates that are suitable for use include: Fe-EDDHA, Cu-EDDHA, Zn-EDDHA, Mn-EDDHA, Sn-EDDHA, and combinations thereof.

The term "heavy metal chelate" refers to an organic coordination "complexing" compound in which a metal ion is bound to atoms of non-metals, e.g., nitrogen, carbon, or oxygen, to form a hetrocylic ring having coordinate covalent bounds. The non-metal atoms may be attached to the metal ions by from one to six linkages and, thus, are called uni, bi, tri dentate, etc., meaning 1-, 2-, or 3-tooth. Heavy metals, such including cobalt, copper, iron, nickel, zinc, tin, magnesium, and platinum, are the metal ions commonly involved in chelate structures. Examples of specific heavy metal chelate structures include:

Fe-HEEDTA (hydroxyethylethylenediaminetriacetic acid), Fe-EDTA (ethylenediaminetetraacetic acid), Fe-DTPA (di-ethylenetriaminepentaacetic acid), Fe-EDDHA (ethylenediamine-di-o-hydroxyphenylacetic acid), ethylene-bis-di-thiocarbamates of Mn and Zn (EBDC), Cu-EDDHA, Mn-EDDHA, and Zn-EDDHA.

To form the heavy metal chelate aqueous composition the heavy metal chelate will be mixed with an amount of aqueous solution. Generally, special treatment of the water is not required, such as deionizing the water for example. Additionally, the mixing will preferably occur under ambient conditions. The heavy metal chelate will be mixed into the water in an amount sufficient to cause the finished composition to equal from about 0.01 pounds to about 2.0 pounds of AI per acre. More preferably, the heavy metal chelate will equal between 0.01 and 0.05 pounds of AI per acre. Typically this means adding the heavy metal chelate to the water in an amount equal to between about 1% and about 5% by weight of the total solution. More preferably, the heavy metal chelate will be added in an amount equal to about 3% by weight of the total solution.

Once the aqueous composition has been formed by thoroughly blending the heavy metal chelate with the water, the aqueous composition is then ready for application to plants, in particular agricultural crops. The aqueous composition is typically easily applied by spraying or other means of distributing the aqueous solution in a sufficient amount to the plants.

The heavy metal chelate must be applied in a sufficient AI amount, without resulting in phytotoxicity. Unacceptably high levels of phytotoxicity result in foliar burn, defoliation and stem die-back, necrosis, plant stunting, or death. Phytotoxicity can be rated on an international scale of 0–10 where 0 is equal to no phytotoxicity and 10 is complete death of the plant. It is preferred if the heavy metal chelate is applied in an amount so that the phytotoxicity is equal to between 0 and 5.

Phytotoxicity rankings of Fe chelates used in foliar applications are as follows: Fe-HEEDTA—most phytotoxic; Fe-EDTA—intermediate phytotoxic, Fe-DTPA—less phytotoxic, and Fe-EDDHA—least phytotoxic. Thus, the Fe-EDDHA is preferred because it is the least phytotoxic while still imparting excellent fungicidal and bactericidal properties.

Heavy metal chelates disclosed herein will have a water solubility acceptable for use in the inventive fungicide and bactericide. For example, the solubility of sequestrene 138 Fe Iron Chelate in pounds per 100 gallons of water, at various temperatures is similar to the present heavy metal chelate in aqueous solution. (Solubility weight/100 gals. $H_2O$) is shown in Table 1 below:

| TEMPERATURE (° C.) | LBS. | OZ. |
|---|---|---|
| 0 | 69 | 11 |
| 10 | 70 | 7 |
| 20 | 75 | 4 |
| 30 | 81 | 11 |
| 40 | 84 | 1 |
| 50 | 88 | 1 |

Commercially produced Sequestrene 138 Fe contains 6% Iron as metallic, or 8.5% iron as $Fe_2O_3$. The commercial product has a moisture content of not more than 10%. As such, this is exemplary of a suitable solubility. Thus, it is desired for the heavy metal chelate, in particular the Cu-EDDHA, to have a solubility of about 100% where at least 80 lbs. of heavy metal chelate is dissolved in 100 gallons of $H_2O$ at 50° C.

Without being limited to this theory, it is believed that heavy metal chelation generally increases the water solubility of the heavy metal ion and the availability in certain soil conditions of the metal ion where calcareous and high pH situations would otherwise prevent metal ions from being available to the plant as a fungicide.

It is believed that certain heavy chelates (usually in the form of Mn, Zn, and Fe) may be applied foliarly at much reduced rates when compared to inorganic salts intended for fungicidal use.

The preferable method of application is foliar, either by ground or aerial equipment, but is not limited to that method alone. Injection or soil applications, for example, can also be used depending upon the specific crops and pathogens.

Among the plants that can be treated with the heavy metal chelate in aqueous solution are: fruit crops, and agronomic crops, ornamentals, trees, grasses, vegetables, grains, and flori-cultural crops, as well as, some aquatic crops, including rice.

The fungicidal and bactericidal properties of the compounds according to the invention are various, but are particularly interesting in the cases described in the following examples.

Figure 1:
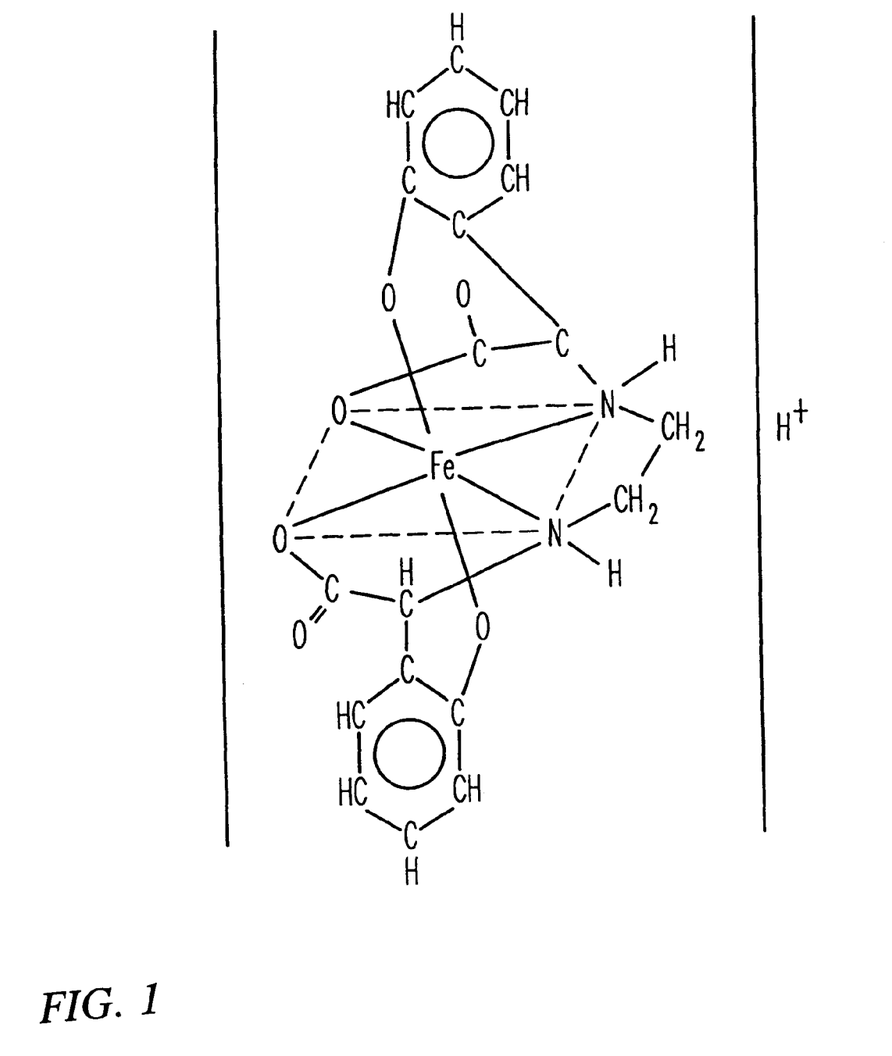
FIG. 1 is a drawing of the chemical structure for Fe-EDDHA (iron chelate of ethylenediamine-di-o-hydroxyphenylacetic acid)
Figure 2:
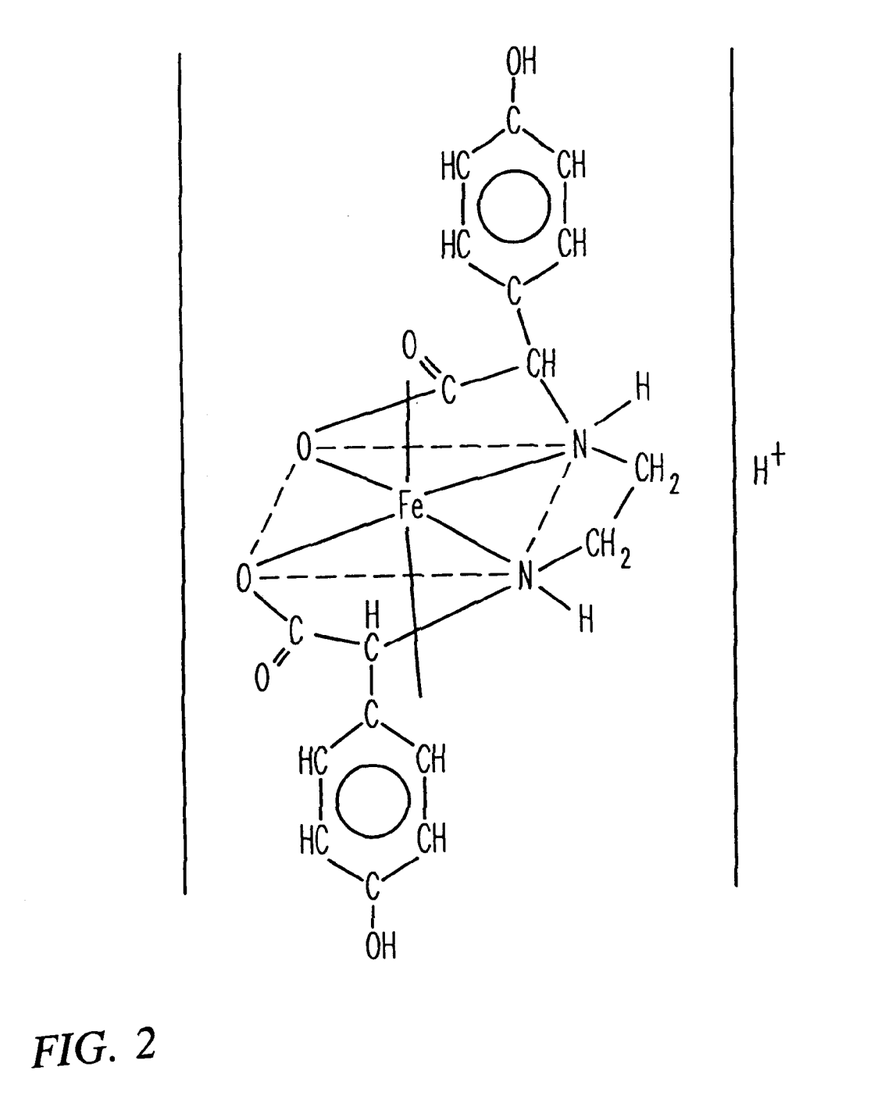
FIG. 2 is a drawing of the chemical structure for Fe-pEDDHA (iron chelate of para-ethylenediamine-di-o-hydroxyphenylacetic acid)
Figure 3:
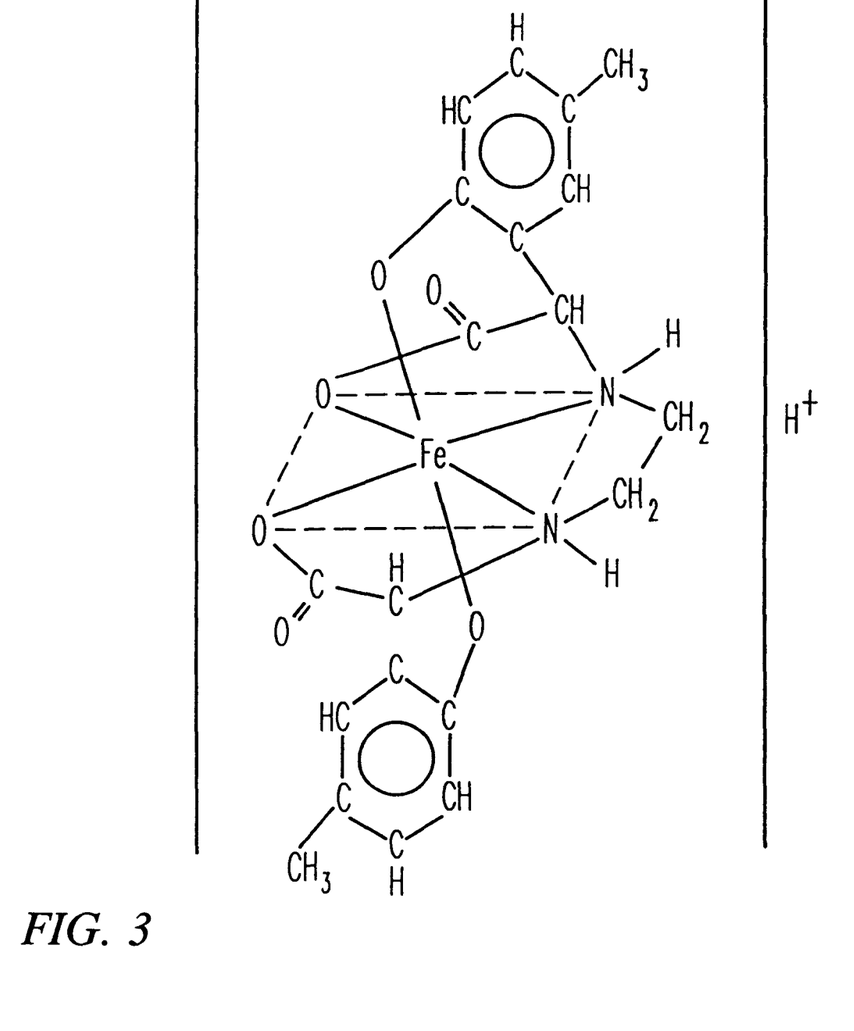
FIG. 3 is a drawing of the chemical structure for Fe-EDDHMA (iron chelate of ethylenediamine-di-o-hydroxyphenylmethylacetic acid); and, FIG. 4 is a drawing of the chemical structure for Cu-EDDHA (copper chelate of ethylenediamine-di-o-hydroxyphenylacetic acid).
Figure 4:
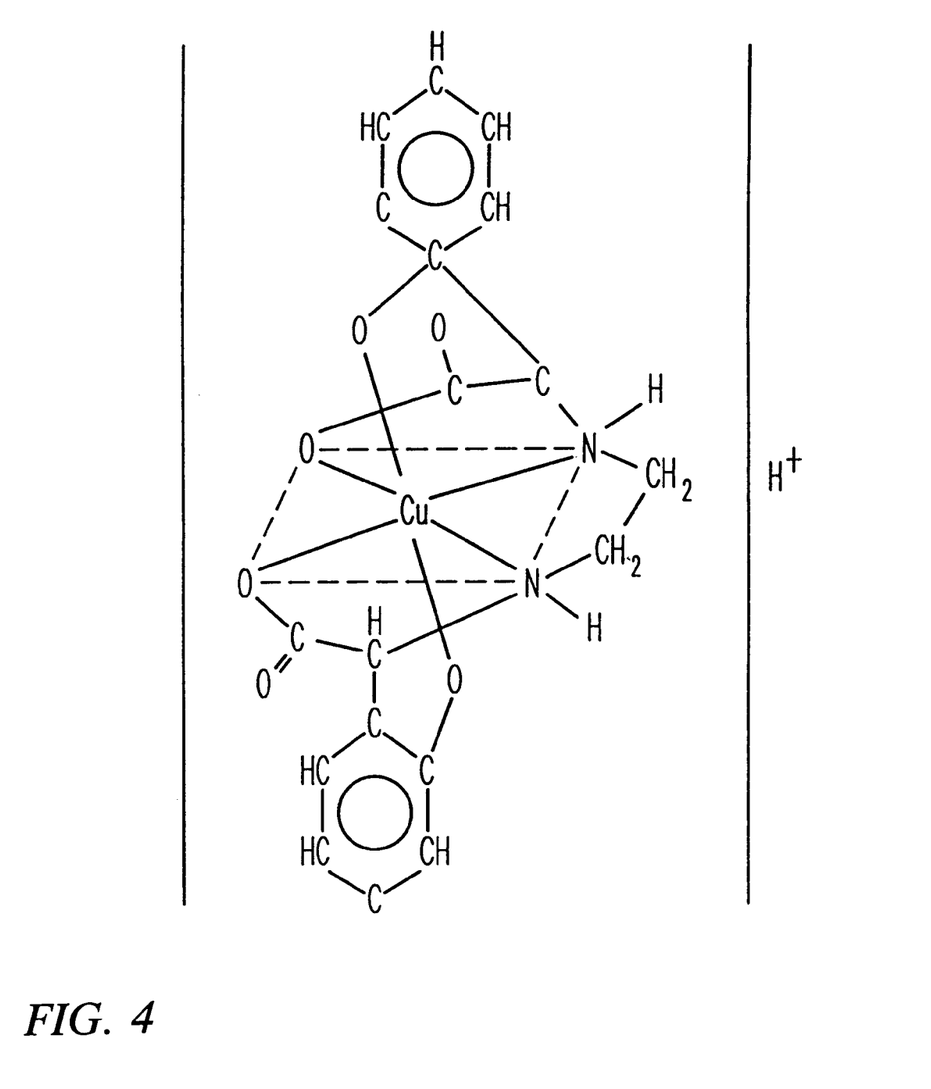

The following examples set forth preferred concentrations and techniques for formulation thereof, as well as methods of application and use in test results, demonstrating the efficacy of the inventive concentration in protecting plants against attack by fungi or bacteria, or both. It is to be understood, however, that these Examples are presented by way of illustration only, and nothing therein shall be taken as a limitation upon the overall scope of the invention. The specific components tested in the Examples were prepared and applied as follows:

To prepare Cu-EDDHA, an appropriate Cu salt need merely be substituted for the iron salts as discussed before and disclosed in U.S. Pat. No. 2,921,847, which is incorporated herein by reference. The chemical structure for Cu-EDDHA is illustrated in FIG. 4. The chemical structures for other common heavy metal chelates are illustrated in the following figures: FIG. 1, Fe-EDDHA; FIG. 2, Fe-pEDDHA; and FIG. 3, Fe-EDDHMA.

As used in the Examples, "Ave. % infection" means percent of leaves that exhibit fungus lesions.

EXAMPLES

Example 1

Cu-EDDHA and four commercially accepted fungicidal compositions were applied to Valencia orange on sour orange rootstock. Applications were in 100 gallons of solution (in the concentrations indicated in the table below) per acre in mid-summer to single-tree plots replicated six times in a randomized complete block ("RCB") design. Seven months later, the percentages of Citrus Greasy Spot infection on five branch terminals from each tree were recorded and averaged.

CITRUS GREASY SPOT TEST CAUKINS
GROVES, INDIANTOWN, FLORIDA

| TREATMENT | RATE/100 GALLONS | *AVE % INFECTION 2/10/88 |
|---|---|---|
| FCC-455 Spray Oil (Florida Citrus Commission) | 1% | 30.0 |
| Difenconazole | 50 gram (gm) ai | 1.56 |
| Difenconazole | 100 gm ai | 1.0 |

-continued

| TREATMENT | RATE/100 GALLONS | *AVE % INFECTION 2/10/88 |
|---|---|---|
| Cu-EDDHA 3.2% | 0.2 lbs. ai | 2.5 |
| KOCIDE 101 | 4 lbs. | 23 |
| Untreated | — | 35 |

APPL. Single tree plots × 6 Reps.
*Aug. 5 terminals/tree

The Difenconazole (triazole): specifically, 1-2[2-[4-(4-chlorophenoxy)-2-chlorophenyl-(4-methyl-1, 3-dioxolan-2-1)-methyl]]-1H-1,2,4-triazole (available from Ciba-Geigy, Greenborough, N.C.) is a triazole fungicide. As can be seen, from the table it provided desirable fungus repression. But, triazole is well known to be potentially hazardous to human health, in particular it is known to be damaging to the human liver.

Also tested, was Cu-EDDHA: (Sodium cupric ethylenediamine-di-o-hydroxyphenylacetic acid), which is the fungicide/bactericide of the present invention. Analysis of the data shows excellent results from applying the Cu-EDDHA.

KOCIDE 101 is a fungicide available from Griffin Corp., Valdosta, Ga. The composition FCC-455 spray is also fungicide. The % infection of the plants treated with the KOCIDE and FCC-455 compositions is considered unacceptable. Also, note that KOCIDE is a copper hydroxide composition.

From the table AVE % infection relates to the percentage infection of Citrus Greasy Spot (*Mycosphaerella citri*) found on the treated leaves.

Example 2

In the present Example, fungicides were again tested on "Valencia" oranges except the effect of various fungicides on perithecia was tested. Three different fungicides, the Cu-EDDHA, TILT (Propiconazole made by Ciba-Geigy), and difenconozole were applied in 100 gallons per acre (gpa) to single tree plots of "Valencia" oranges replicated five times in a RCB design in mid-July.

Twenty mature leaves (from the spring flush) per replicate were harvested approximately 4 months later and placed under greenhouse conditions and alternately wetted and dried to simulate natural defoliation and weathering.

These conditions, in turn, cause the fungus to sporulate by the formation of perithecia (spore production body of fungus). The spores were counted as a means of measuring the fungicidal activity of the treatments. The data is presented below.

CITRUS GREASY SPOT SCN NURSERY,
DUNDEE, FLORIDA

| TREATMENT | RATE/100 GALLONS | # PERITHECIA |
|---|---|---|
| Cu-EDDHA 3.2% | 0.2 lbs. ai | 3.24 b |
| Cu-EDDHA 3.2% | 0.4 lbs. ai | 5.93 ab |
| TILT 3.6 EC | 6 oz. Prod. | 6.62 ab |
| Difenconazole | 100 gm ai | 5.32 ab |
| Difenconazole | 200 gm ai | 11.57 ab |

-continued

| TREATMENT | RATE/100 GALLONS | # PERITHECIA |
|---|---|---|
| CONTROL inoculated | | 7.97 ab |
| CONTROL not inoculated | | 6.42 ab |

The conditions of the test were as follows:
  Function: ANOVA—1
  Date Case No. 1 to 42
  Without selection
  One way ANOVA grouped over variable 1
  TREATMENT NUMBER
  With values from 1 to 7
  Variable 3
  NUMBER OF PERITHECIA PER 5 MM FIELD AT 2.5 X—MEAN OF THREE
  OBSERVATIONS
  a, b, and ab indicate statistical significance.

The tests produced important data because if the perithecia is reduced then it follows that the number of infections are reduced. The Cu-EDDHA showed good results. The TILT also showed decent results, but is not preferred because it has limited uses as promulgated by the FDA (Food and Drug Administration). Also, note that Cu-EDDHA added in a higher AI did not result in enhanced repression of the perithecia. This seems to indicate that if too much Cu-EDDHA is added, slight phytotoxicity will result.

ANALYSIS OF VARIANCE TABLE

| | DEGREES OF FREEDOM | SUM OF SQUARES | ERROR MEAN SQUARE | F-VALUE | PROB. |
|---|---|---|---|---|---|
| Between | 6 | 226.6508 | 37.78 | 1.33 | .270 |
| Within | 34 | 965.0170 | 28.38 | | |
| Total | 40 | 1191.6678 | | | |

Example 3

Cu-EDDHA, KOCIDE (cupric hydroxide), and difenconazole were applied to single tree plots of "Hamlin" oranges in 100 gpa (in concentration indicated) in a RCB design replicated 4 times. Applications were made in either May, June or May, and June. Ten fruit/replicates were sampled in July and percent infection of Melanose (Diaporthe citri) was determined. See data presented below.

CITRUS MELANOSE CONTROL R.E. KEENE FRUIT COMPANY

| TREATMENT | RATE LB AI/100 GALLONS | TIMING | % INFECTION (FRUIT) |
|---|---|---|---|
| Cu-EDDHA 3.2% | 0.2 | May | 9 |
| Cu-EDDHA 3.2% | 0.4 | May | 13 |
| Cu-EDDHA 3.2% | 0.8 | May | 21 |
| Cu-EDDHA 3.2% | 0.2 | May–June | 11 |
| Cu-EDDHA 3.2% | 0.4 | May–June | 15 |
| Cu-EDDHA 3.2% | 0.8 | May–June | 29 |
| Cu-EDDHA 3.2% | 0.2 | June | 14 |
| KOCIDE | 4.0 | May | 12 |
| KOCIDE | 0.4 | May–June | 10 |
| DIFENCONAZOLE | 0.5 | June | 4 |
| Untreated | — | — | 38 |

4 REPS SINGLE TREE PLOTS.
PENETRATOR (surfactant—non-ionic) @ 4 oz. ALL TREATMENTS The results indicate that in general not too much Cu-EDDHA should be applied to the plants. Also, an appropriate application time of year such as May, should be chosen.

Example 4

In the present example, GRAPEFRUIT plants (*Citrus paradisi* 'Marsh') were tested with various fungicides to determine the effectiveness in eliminating greasy spot, *Mycosphaerella citri*.

Spray treatments were applied dilute (applied to point of run off) by handgun in July to 10-foot high trees at a rate equivalent to 700 gpa. Treatments were replicated on 8 single tree plots in a RCB design. Groups of 15 shoots on each of the east/west and east side of each tree were tagged and the initial number of leaves was recorded. In February, remaining leaves were counted and examined for greasy spot.

| TREATMENT AND RATE/100 GALLONS | DEFOLIATION | % REMAINING LEAVES WITH GREASY SPOT |
|---|---|---|
| Tribasic copper sulfate (53% Cu) 0.75 lb. | 1.9 a | 20.1 a |
| Sunspray 7E oil 1 gal. | 3.1 a | 27.0 a |
| Difolatan 80 Sprills 1.25 lb. | 8.9 b | 49.8 b |
| Spotless 25W 0.8 lb | 1.3 a | 22.6 a |
| Tilt 3.6EC 8 fl. oz. | 1.5 a | 15.9 a |
| Cu-EDDHA (3.2% Cu) 1.5 gal. | 0.8 a | 12.0 a |
| Untreated | 9.7 b | 48.5 b |

All treatments, except Difolatan (fungicide), reduced greasy spot-induced defoliation and the percentage number of remaining leaves with greasy spot symptoms. There were no significant differences in effectiveness between Tribasic copper sulfate, spray oil, Spotless, Tilt, and Cu-EDDHA. There was too little greasy spot rind blotch in this test to provide information on the relative efficacy of treatments for preventing fruit infection.

Copper sulfate is phytotoxic so that it needs to have its phytotoxicity reduced. This is accomplished by combining CaOH with the $CuSO_4$. Unfortunately, this reduces solubility.

Example 5

Cu-EDDHA, TILT (propinconazole), difenconazole, and MERTECT ((Merck Chem., N.J.) thiabendazole)) were applied in 100 gpa to 2-year-old laurel oaks (*Quercus hemispherica*) in 2×2 gal. pots in a RCB design replicated 4 times. MERTECT is a standard well known fungicide that does not include copper. Applications were made in July approximately 3 weeks apart and rated in August a month later. See data below.

OAK LEAF BLISTER (*Taphrina Caerulescens*)
CONTROL TRAILRIDGE NURSERY,
KEYSTONE HEIGHTS, FLORIDA

| TREATMENT | RATE/PRODUCTION 100/GALLONS | *DISEASE INDEX |
|---|---|---|
| Tilt 3.6 emulsifiable | 8 oz. | 1.5 |
| Difenconazole 3.6 emulsifiable | 2 oz. | 2.25 |
| Cu-EDDHA 3.2 | 8 oz. | 2.8 |
| MERTECT | 8 oz. | 1.5 |
| Untreated | — | 4.25 |

*Disease Index: Rated 8/26/86.
1 = no disease
2 = light
3 = moderate
4 = heavy
5 = dead foliage 2×2 gal. trees/exp. unit×4 Reps in a RCB design As can be seen, suitable disease repression occurred with the Cu-EDDHA composition, even though the concentration would be considered a bit high.

Example 6

Cu-EDDHA and Kocide (cupric hydroxide) were applied as foliar spray in May to *Hibiscus sinensis* cuttings (100/replicate)×4 replicates in a RCB design. Treatments were allowed to dry for one hour and then placed in a commercial propagation bed under intermittent mist and rated for bacterial (*Erwinia chrysanthemi*) infection one week later. Data is presented below:

*ERWINIA CONTROL ON HIBISCUS NELSONS
NURSERY, APOPKA, FLORIDA

| TREATMENT | RATE/CU 100/GALLONS | AVERAGE % INFECTION |
|---|---|---|
| Cu-EDDHA 3.2% | 0.2 lb. ai | 6 |
| Cu-EDDHA 3.2% | 0.4 lb. ai | 8 |
| Kocide 101 | 2 lbs. ai | 25 |
| Untreated | — | 100 |

100 Cuttings/REP×4 *ERWINIA Chrysanthemi

The Cu-EDDHA added in an amount equal to 0.2 lb. AI showed excellent control of Erwina on Hibiscus.

Example 7

A follow-up experiment to Example 6 was conducted on rooted cuttings which were dipped as they were removed from the propagation bed and foliarly sprayed 7 days later after being potted. Cu-EDDHA and Kocide were applied at the rates specified below in a RCB design utilizing 100 plants/replicate×4 reps. Potted cuttings had not received any previous bactericide treatments prior to potting.

ERWINIA CONTROL ON HIBISCUS NELSONS
NURSERY—APOPKA, FLORIDA

| TREATMENT | RATE/LB. AI 100/GALLONS | AVERAGE % INFECTION |
|---|---|---|
| Cu-EDDHA 3.2% | 0.2 | 19 |
| Cu-EDDHA 3.2% | 0.8 | 32 |
| KOCIDE | 2.0 | 22 |

APPLIC. DATES: July 19 DIP, Jul. 26, 1985 SPRAY 100 PLANTS/REP.×4

Again excellent control was achieved with Cu-EDDHA applied in an amount equal to 0.2 lb. AI.

Example 8

The present Example relates to controlling bacterial spots on pepper plants. The procedure for the present Example was as follows: Early Cal Wonder variety pepper plants were treated at weekly intervals with the following bactericides (g AI/liter in parentheses): copper+mancozeb (2+1), Cu-EDDHA (0.1), CGA (Ciba Geigy American)-115944, CGA-151731, CGA-157566, and CGA-164058 (each at 0.25 and 0.5), CGA-143268 (1.0). Treatments were applied weekly in 1000 l/ha for a total of eight applications. The crop was artificially inoculated after the first and third applications. Disease severity was evaluated after the fourth and eight applications. Phytotoxicity was rated after the eight application and yields were taken continually during the test.

The results of the testing were determined as such: Disease pressure was moderate and uniform. After four applications, the best treatments were CGA-115944, CGA-151731, and CGA-164058. CGA-157566 was less effective than the three previously mentioned compounds, but more effective than CGA-143268 which was equal to copper plus mancozeb and Cu-EDDHA in activity. The ranking of compounds changed when treatments were rated 12 days after the last application. Copper plus mancozeb control has completely broken down, which was expected because disease conditions were severe in the final half of the test and copper should be applied on a five-day schedule under these conditions. Cu-EDDHA at only 0.05× the rate of Kocide 101 (on a metallic copper basis) was exhibiting some control and was equal to CGA-143268, CGA-157566, and CGA-164058. The best bactericide at the second rating were CGA-115944 and CGA-151731. The phytotoxicity of all treatments was assessed after eight applications had been made. The only bactericides which were phytotoxic were CGA-115944 and CGA-164058. CGA-164058 was safer than CGA-115944, which was marginally unacceptable at 0.5 AI/l. CGA-1443268 and CGA-164058 increased yields dramatically. Yields were depressed by CGA-0115944, CGA-151731, and CGA-157566. Cu-EDDHA had no effect on yield and copper+mancozeb increased yields moderately. In summary, several compounds showed excellent activity, but none had sufficient crop safety.

Example 9

Croton plants inoculated with Xanthomonas were tested with various fungicides. Cu-EDDHA at 0.2 and 0.4 lbs. ai/100 gal. and Kocide 101 at 7.4 lbs. AI/Acre (A) were applied as foliar applications to croton (*Codiaeum variegatum*) previously inoculated with *Xanthomonas campestris* a day earlier. Treatments were assigned in a RCB design and replicated 10 times with single pots. Treatments were applied 3 times on a weekly schedule and evaluated at 7 and 14 days following the last application. See data below.

Test 1 Codiaeum Inoculated with Xanthomonas
Number of leaves with symptoms

| TREATMENT | RATE/100 GALLONS AI. | AVERAGE % OF INFECTION |
|---|---|---|
| Water | noninoculated | 0 a |
| Water | inoculated | 2.6 c |
| Cu-EDDHA 3.2% | 26 ml (.2 lb.) | .6 ab |
| Cu-EDDHA 3.2% | 52 ml (.4 lb.) | 1.0 b |
| Kocide 101 | 6.8 ml. (7.4 lb.) | .9 ab |

ANOVA table

| SOURCE | SUM OF SQUARES | DF | MEAN SQUARE | F VALUE |
|---|---|---|---|---|
| Treatment | 37.28 | 4 | 9.319 | 9.177 significant at 1% level |
| Error | 45.7 | 45 | 1.016 | |
| Total | 82.98 | 49 | | |

It was determined that all of the copper treatments provided some control of Xanthomonas leaf spot of Codiaeum, when compared to the inoculated control. The lower rate of Cu-EDDHA and the Kocide 101 gave control equal to the noninoculated control treatment.

Example 10

In the present example, carrots were inoculated with the Alternaria fungus. The carrots were then treated with the below listed fungicidal compositions. Also a control test was conducted. The percentage of the fungicide in the solution is also listed below along with the results. Plot size for testing was a single row of 25 feet by 4 repetitions in an RCB design. The fungicide was applied eight (8) times with the carrots then examined for infection seven (7) days and thirty (30) days after the last fungicidal treatment.

CARROT/ALTERNARIA FUNGICIDE TRIAL

| | | RATE/100 | AVERAGE % OF INFECTION | |
|---|---|---|---|---|
| | TREATMENT | GALLONS | 04/05/96 | 04/23/96 |
| 1) | K-PHOS | 1% | 6.9 | 8.2 |
| 2) | PHOS-MIGHT | 1% | 18.7 | 28.8 |
| 3) | K-PHOS + PHOS-MIGHT | 0.5% + 0.5% | 8.9 | 10.7 |
| 4) | Cu-EDDHA | 0.2 lb ai | 8.8 | 11.6 |
| 5) | Fe-EDDHA | 0.2 lb ai | 12.7 | 12.9 |
| 6) | CONTROL | — | 23.0 | 34.8 |

*EDDHA (Ethylenediamine-di-o-hydroxyphenylacetic acid)

PLOT SIZE: Single Row×25 ft. ×4 reps in a RCB design.

Application dates: Febuary 2, 9, 15, 22, March 8, 14, 22, and 28. Rated April 5 and Apr. 23, 1996

NOTE: Second rating was 25 days after last fungicide application. Plots were inoculated with *Alternaria dauci.*

The tests were conducted in Sanford, Fla.

K-PHOS ($KH_2PO_4$, 0-18-20) is a commercially available phosphate fungicide and fertilizer composition. The PHOS MIGHT ($KH_2PO_3$, 0-22-20) is a commercially available phosphonate fungicide and fertilizer composition.

As can be seen, Cu-EDDHA effectively limited percentage of fungicidal infection. It can be concluded that the Cu-EDDHA as well as the Fe-EDDHA are effective for controlling fungicides.

The above Examples demonstrate that the inventive compositions are useful in protecting plants against attack by fungus with the application of the inventive solution.

It will be further appreciated that foliar application of the inventive compositions will be effective as a common agricultural practice to control bacterial infections in plants.

It will be appreciated by those skilled in the art that beneficial effects demonstrated in the Examples by the use of Cu-EDDHA will also be obtained when the Mn, Sn, Fe, and Zn EDDHA form heavy metal chelates are employed.

Thus, there has been shown and described a method of use for fungicidal and bactericidal compositions, which provide improved efficacy in controlling fungi and bacterial infections in plants. More particularly, the compositions and method related to heavy metal chelates, and preferably a copper chelate in the form of Cu-EDDHA (copper sodium cupric ethylenediamine-di-o-hydroxyphenylacetic acid), in an aqueous solution, which fulfills all the objects and advantages sought therefore. It is apparent to those skilled in the art, however, that many changes, variations, modifications, and other uses and applications for the subject fungicidal and bactericidal compositions are possible and, also, such changes, variations, modifications, and other uses and applications which do not depart from the spirit and scope of the invention are deemed to be covered by the invention which is limited only by the claims which follow.

What is claimed is:

1. A method for controlling fungal and/or bacterial disease wherein said method comprises applying to a plant that is infected with a fungal and/or bacterial disease a composition comprising a fungicidally and/or bactericidally effective amount of a heavy metal chelate in an aqueous solution, wherein the heavy metal chelate has low or no phytotoxicity to plants, wherein the heavy metal is selected from the group consisting of zinc, tin, manganese, copper, and combinations thereof, wherein the chelate is selected from the group consisting of EDDHA, pEDDHA, EDDHMA and combinations thereof, and wherein the heavy metal chelate is present in an amount between 1% and 5% by weight of the aqueous solution and is applied at a rate of about 0.1 to about 2.0 pounds of said heavy metal chelate per acre.

2. The method of claim 1 wherein the heavy metal chelate has a solubility equal to about 100% where at least 80 pounds of said heavy metal chelate is dissolved in 100 gallons of water at 50 degrees Celsius.

* * * * *